(12) United States Patent
Meiman, Jr.

(10) Patent No.: US 9,903,793 B1
(45) Date of Patent: Feb. 27, 2018

(54) APPARATUS AND METHOD TO REDUCE BIOFOULING OF WATER QUALITY DATASONDES

(71) Applicant: Joseph John Meiman, Jr., Park City, KY (US)

(72) Inventor: Joseph John Meiman, Jr., Park City, KY (US)

(73) Assignee: The United States of America as Represented by the Secretary of the Department of the Interior, Washington, DC (US)

(*) Notice: Subject to any disclaimer, the term of this patent is extended or adjusted under 35 U.S.C. 154(b) by 241 days.

(21) Appl. No.: 14/936,575

(22) Filed: Nov. 9, 2015

(51) Int. Cl.
*G01N 1/14* (2006.01)
*G01N 33/18* (2006.01)

(52) U.S. Cl.
CPC ........... *G01N 1/14* (2013.01); *G01N 33/1886* (2013.01)

(58) Field of Classification Search
CPC .............................. G01N 1/14; G01N 33/1886
See application file for complete search history.

(56) References Cited

U.S. PATENT DOCUMENTS

| | | | | |
|---|---|---|---|---|
| 3,949,612 A | * | 4/1976 | Thompson | G01N 1/14 417/145 |
| 4,314,969 A | * | 2/1982 | Arthur | G01N 33/1806 422/79 |
| 4,763,537 A | * | 8/1988 | Scott | G01N 33/1886 396/26 |
| 6,197,256 B1 | | 3/2001 | Siepmann | |
| 7,437,248 B2 | * | 10/2008 | Sihalla | G01N 1/14 702/22 |
| 7,542,855 B2 | | 6/2009 | Sihalla | |

OTHER PUBLICATIONS

"LDM Anti-fouling Module" Hydrotechzs.com. Hydrotech ZS Consulting, n.d. Web. http://www.hydrotechzs.com/products/ldm-anti-fouling-module.html.

* cited by examiner

*Primary Examiner* — Paul West
*Assistant Examiner* — Xin Zhong
(74) *Attorney, Agent, or Firm* — James Mitchell

(57) ABSTRACT

An apparatus and method for controlling biofouling of a datasonde. The apparatus includes a sample chamber that attaches to the end of the datasonde and encloses its sensor array. The sample chamber is plumbed with a water tube that allows ambient water to flow into and out of the sample chamber. The chamber is also plumbed with an air tube that allows air to flow into and out of the sample chamber. The air tube is split above the water surface with each side having an in-line solenoid valve. One side of the air tube is connected to a compressed air source and the other side is open to the atmosphere. Compressed air is introduced to the sample chamber at set intervals, forcing extant sample water from the sample chamber via the water tube to control biofouling of the sensor array.

19 Claims, 4 Drawing Sheets

APPARATUS AND METHOD TO REDUCE BIOFOULING OF WATER QUALITY DATASONDES

STATEMENT OF GOVERNMENT INTEREST

The invention described herein may be manufactured, used, and licensed by or for the U.S. Government for governmental purposes without payment of any royalties thereon.

BACKGROUND

The present invention relates in general to aquatic monitoring devices and, more particularly, to reducing biofouling of aquatic monitoring devices.

Datasondes are commonly deployed in aquatic environments to collect multi-parameter water quality data. These aquatic environments often present conditions that lead to pervasive biofouling of the datasonde's sensors. Biofouling reduces the quality of the data collected because the fouling organisms interfere with the function of the sensors. In addition, the concentrated activity of the biofouling organisms may impact the sensors' ability to monitor the ambient water quality by creating a microenvironment in the immediate vicinity of the sensors. To maintain sample integrity in extended datasonde deployments in high biofouling environments, frequent maintenance is necessary to manually clean and recalibrate the datasonde and its sensors. This level of maintenance is costly and in remote deployments, can be cost prohibitive. In the majority of aquatic datasonde deployments, biofouling is often the single biggest factor affecting operation, maintenance, and data quality.

Various technologies have been utilized to respond to biofouling with limited success. Most advancements have been in cladding of datasondes in copper or coating the datasonde with anti-bio-fouling paint. While such applications make for an easier cleanup it does little to reduce bio-fouling at the sensor interface because a pH sensor or optical window cannot be painted or plated with copper. To date, biofouling prevention has not been adequately addressed and continues to present a major challenge and cost in aquatic environment monitoring.

There is therefore a need for an aquatic monitoring apparatus that reduces or resists biofouling of multiparameter datasondes, which will result in increased data quality, extended deployments, and less datasonde maintenance.

SUMMARY

An aquatic monitoring apparatus is described herein that extends deployment periods of multi-probe datasondes by reducing biofouling.

The present invention includes a sample chamber that attaches to the end of a datasonde and encloses the datasonde's sensor array. The sample chamber is plumbed with two ports: 1) a water tube that allows direct communication between the sample chamber and the ambient hydraulic environment, and 2) an air tube that facilitates the filling and purging of ambient water in the sample chamber. While the water tube is a simple portal between the sample chamber and the surrounding hydraulic environment, the air tube bifurcates within an instrument case above the water with one side ported to the atmosphere and the other side connecting to a compressed air source. In-line solenoids control the status (open/close) of the air port, thus the status of the sample chamber (full/purged).

Timing events with a datalogger or other controller allows for the datasonde's sensor array to be submerged in ambient water inside the sample chamber during sample times and then the sample chamber is purged of ambient water after the sample is recorded. When the sample chamber is purged of ambient water, the sensor array remains moist (100% relative humidity) due to residual moisture in the sample chamber but is not submerged.

As long as the sensors are in contact with water they are subject to biofouling. The less time a sensor is in contact with high bio-fouling water, the less bio-fouling will occur on the sensor, thus extending the deployment period and reducing service intervals. By limiting the time that the sensor array is submerged, the instance of biofouling is significantly reduced and in some cases, effectively eliminated.

In accordance with an embodiment of the invention, there is provided an aquatic monitoring apparatus for use in controlling biofouling of a water sensing device. The aquatic monitoring apparatus includes a water sensing device having a sensor array. A sample chamber is attached to the water sensing device that encloses the sensor array. A water tube projects out of the sample chamber and into a body of water to be sampled. An air tube has a first end that projects into the sample chamber and a second end that extends above the body of water. An air source is connected to the second end of the air tube. A controller is connected to the water sensing device and the air source to control the water sensing device, the air source, and sampling of the water during sample cycles. The water enters and fills the sample chamber through the water tube and contacts the sensor array. The water entering the sample chamber displaces the air inside the sample chamber, which escapes into the atmosphere through the air tube. The controller then operates the water sensing device to sample the water. Once the water has been sampled, the controller activates the air source to force air into the sample chamber through the air tube to purge the sample chamber of the water so that the sensor array does not remain immersed in biofouled water.

In accordance with another embodiment of the invention, there is provided a method for controlling biofouling of a water sensing device. The method includes providing a water sensing device having a sensor array and attaching a water-tight sample chamber to the water sensing device that encloses the sensor array. A water tube is provided that projects out of the sample chamber and into a body of water to be sampled. An air tube is provided that projects out of the sample chamber and extends above the body of water. The sample chamber is filled to sample the body of water by allowing the water to enter the sample chamber through the water tube and contact the sensor array while air inside the sample chamber escapes into the atmosphere through the air tube. Once the water has been sampled, biofouling is controlled by forcing air into the sample chamber through the air tube which purges the sample chamber of the water so that the sensor array does not remain immersed in biofouled water.

In accordance with another embodiment of the invention, there is provided a method for using water measuring probes of a water sensing device to measure predetermined characteristics of water proximate to the probes. The method includes providing a water-sealed sampling chamber enclosing the probes from the water proximate to the water sensing device. The sampling chamber is constructed to be submerged in a body of water of which the predetermined characteristics of water are to be measured. An air tube is provided that connects the sampling chamber to outside air above the body of water and enables a flow of air between the sampling chamber and the outside air above the body of water. An air input device is provided for selectively forcing air into the sampling chamber. An air output device is provided to vent air out of the sampling chamber to the atmosphere above the body of water. An amount of air in the sampling chamber is controlled wherein water is only in contact with the probes when the probes are measuring the predetermined characteristics of water in the sampling chamber.

BRIEF DESCRIPTION OF THE DRAWINGS

Various aspects and advantages of the invention will become apparent from the following detailed description, taken in conjunction with the accompanying drawings. The drawings are not necessarily drawn to scale. In the drawings.

DETAILED DESCRIPTION

Figure 1:
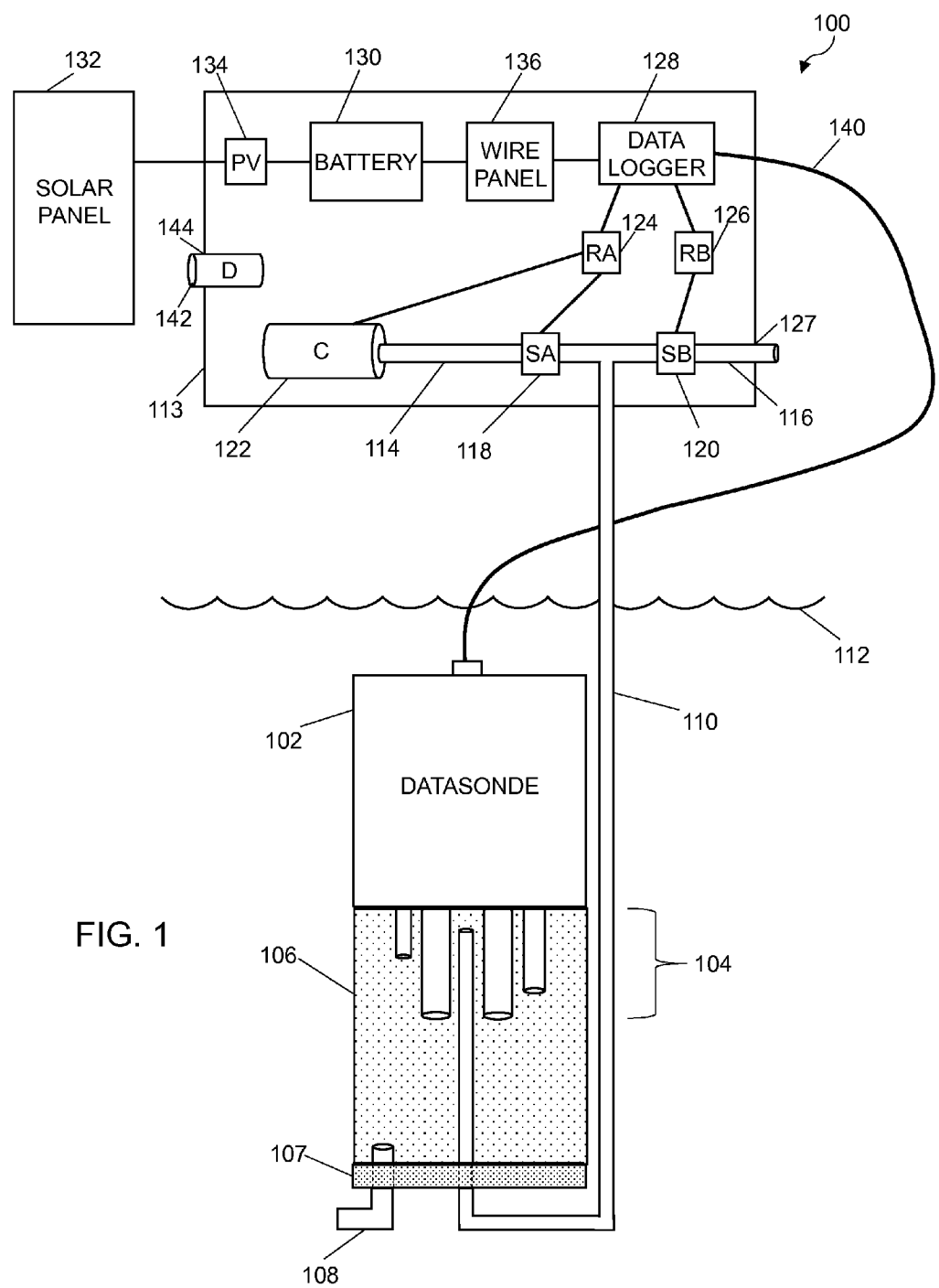
FIG. 1 illustrates an aquatic monitoring apparatus at a state between sample times with a sample chamber that is free of water, according to an embodiment of the invention.

Referring to FIG. 1, an aquatic monitoring apparatus 100 is shown that reduces biofouling of multi-parameter aquatic sensors, according to an embodiment of the invention. The aquatic monitoring apparatus 100 includes a water sensing device such as a datasonde 102 with a sensor array 104 that is submerged under a body of water to be sampled. The datasonde 102 may be, for example, a YSI 6600 datasonde manufactured by YSI, Inc. of Yellow Springs, Ohio. The sensor array 104 may include, for example, temperature, conductivity, pH, and optical turbidity and optical dissolved oxygen sensors.

A sample chamber 106 with an end cap 107 is attached to the datasonde 102 and encloses the sensor array 104. The sample chamber 106 is plumbed with a water tube 108 to allow for the flow of ambient water into and out of the sample chamber 106. The water tube 108 may be constructed, for example, from ½-inch copper tubing. The sample chamber 106 is also plumbed with an air tube 110 to allow for the flow of air into and out of the sample chamber 106. The sample chamber 106 may be constructed, for example, using a datasonde calibration cup with ports constructed in the cup's end cap or calibration cup side to receive the water tube 108 and the air tube 110. A custom designed sample chamber can be used in lieu of a pre-manufactured calibration cup 106 and end cap 107. In addition the air tube 110 may be ported through a side wall of the sample chamber 106 if necessary to place a terminus of the air tube 110 at an elevation higher than the sensor array 104. A weight (not shown) may be hung from a bottom of the end cap 107 to eliminate positive buoyancy while air-filled.

The air tube 110 extends out of the sample chamber 106, above a surface of the body of water 112, and enters an instrument case 113 where it splits into two separate lines 114 and 116. The air tube 110 may be constructed of, for example, ¼-inch copper tubing below the water surface 112 and ⅜-inch braided nylon above the water surface 112. Each line 114 and 116 of the air tube 110 is connected respectively to air-flow solenoid valves SA 118 and SB 120. The end of line 114 connects to a compressed air source C 122, and the end of line 116 is open to the atmosphere through a port 127 in the instrument case 113. Normally closed solenoid valves SA 118 and SB 120 are controlled respectively by relay switches RA 124 and RB 126, which receive commands from a datalogger 128. The datalogger 128 may be, for example, a CR1000 datalogger manufactured by Campbell Scientific, Inc. of Logan, Utah. The datalogger 128 controls the sampling interval and serves as an external data storage/communication platform. The datalogger 128 is connected to the datasonde 102 through a communication cable 140, such as a serial data interface at 1200 baud (SDI-12) communication cable. Other communication methods can be used for communication between the datalogger 128 and the datasonde 102.

The compressed air source C 122, which is controlled by the relay RA 124, may be either an air tank or an air compressor such as a 12-volt DC air compressor. If an air tank is used, it may be, for example, a scuba tank. The air tanks are fitted with a dual stage pressure regulator to control outlet pressure regardless of ambient temperature or tank pressure to the solenoid valve SB 120.

The aquatic monitoring apparatus 100 is powered by a battery 130. The battery 130 is connected to a solar panel 132 through a photovoltaic controller PV 134. The solar panel 132 recharges the battery 130. The battery 130 may be, for example, a 12V, 12 AH rechargeable sealed lead acid battery using compressed air tanks. Alternatively, the battery 130 may be a 12V, 35 AH rechargeable sealed lead acid battery using a 12V compressor and a 10 W solar panel. Other power sources may be used. Power from the battery 130 is fed to the datalogger 128, the solenoids SA 118 and SB 120, and the relays RA 124 and RB 126 through a wire panel 136. Detailed power connections to solenoids and relays are standard practice and not shown in the drawings to promote clarity.

The solenoid valves SA 118 and SB 120, the relays RA 124 and RB 126, the compressor C 122, the datalogger 128, the battery 130, the photovoltaic controller PV 134, and the wire panel 136 are housed in the instrument case 113. A desiccant tube D 142 keeps the instrument case 113 dry through a port to atmosphere 144 in the instrument case 113. The port to atmosphere 144 is also used if the compressor C 122 is electric. The instrument case 113 and the solar panel 132 are located above the water surface 112. If air tanks are used as the compressed air source, there is no need for the atmosphere port 144 or the desiccant tube 142.

FIG. 1 illustrates the aquatic monitoring apparatus 100 in a purged state in which the sample chamber 106 is free of water and filled with air. Considering a 15-minute sample interval for illustrative purposes, the sample chamber 106 is free of water and full of air during the first 14 minutes of the 15-minute interval sample cycle, except for a minimal amount of residual moisture that keeps the sensor array 104 well preserved. At this point, the relays RA 124 and RB 126 are both inactive and the solenoid valves SA 118 and SB 120 are both closed. All timing can be modified to fit a specific datasonde, sensor warm-up time requirements, or other monitoring needs by changing time intervals in the datalogger program.

Figure 2:
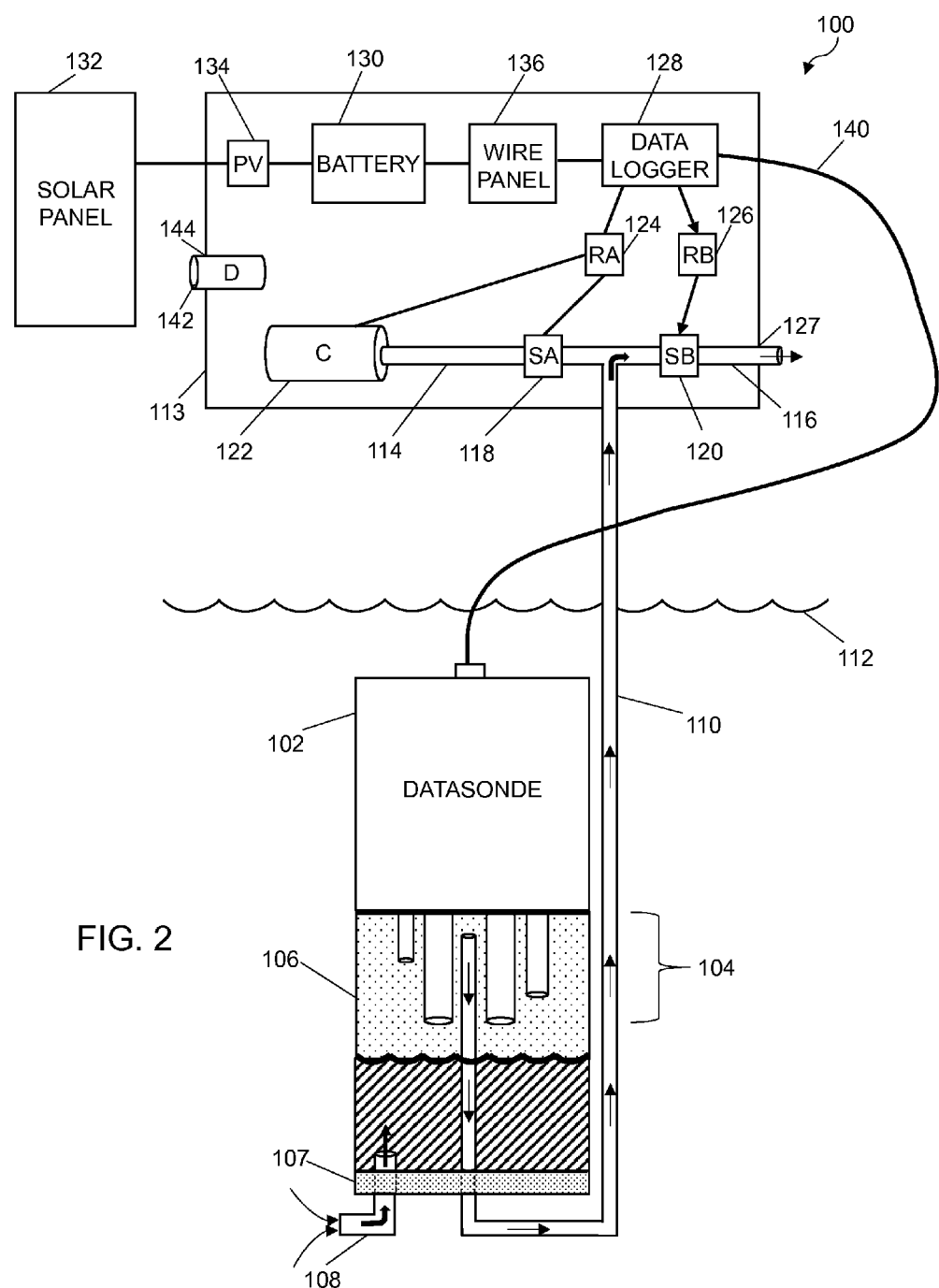
FIG. 2 illustrates the aquatic monitoring apparatus of FIG. 1 immediately prior to a sample time where the sample chamber is being filled with water to be sampled.

FIG. 2 illustrates the aquatic monitoring apparatus 100 as the sample chamber 106 is filling with ambient water. At approximately 14 minutes into the 15-minute sample cycle, the datalogger 128 activates the relay RB 126 to open the solenoid valve SB 120. With the solenoid valve SB 120 open, ambient water enters through the water tube 108 and displaces the air inside the sample chamber 106, which escapes into the atmosphere through the air tube 110 and the line 116. After approximately five to ten seconds, depending on the depth of the datasonde 102, the datalogger 128 deactivates the relay RB 126, which closes the solenoid valve SB 120, and the sample chamber 106 remains filled with water to be sampled. When considering a 15-minute sample interval, the solenoid valve SB 120 is opened at approximately 14 minutes and then the solenoid valve SB 120 is closed at approximately 14 minutes and 10 seconds. These timings will vary depending on datasonde 102 specifications and characteristics of the ambient water.

Figure 3:
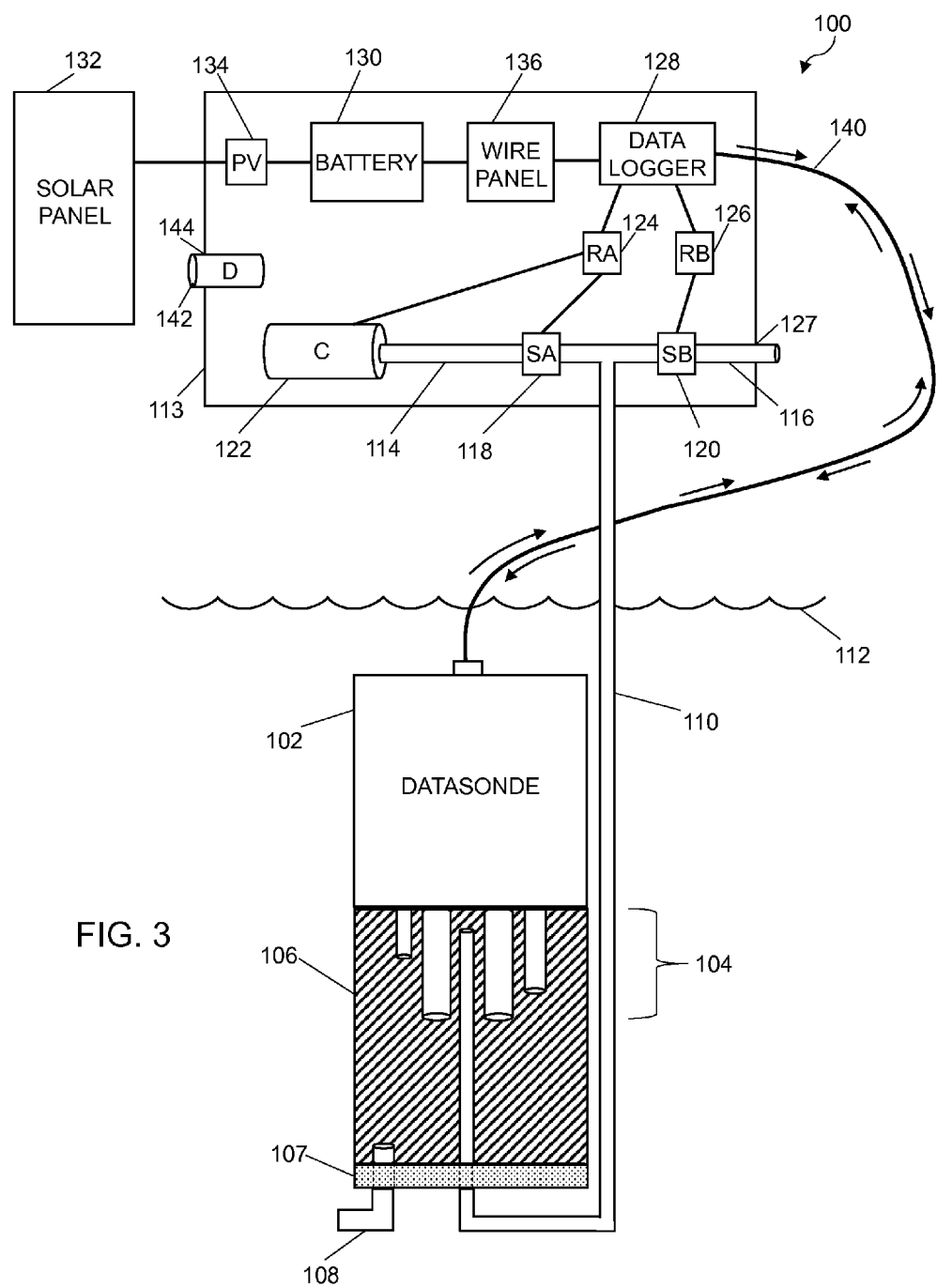
FIG. 3 illustrates the aquatic monitoring apparatus of FIG. 2 during a sample time where the sample chamber is completely filled with water to be sampled.

FIG. 3 illustrates the aquatic monitoring apparatus 100 in a filled state and ready for a sample to be taken. At this stage, the relays RA 124 and RB 126 are inactive and the solenoid valves SA 118 and SB 120 are both closed. With the sample chamber 106 filled with ambient water, the datalogger 128 initiates a sampling event to the datasonde 102. When considering a 15-minute sample interval, the sampling event is initiated at approximately 15 minutes. At that time, the sensor array 104 has been in contact with ambient water for approximately one minute. The sampling event takes approximately 35 seconds.

Figure 4:
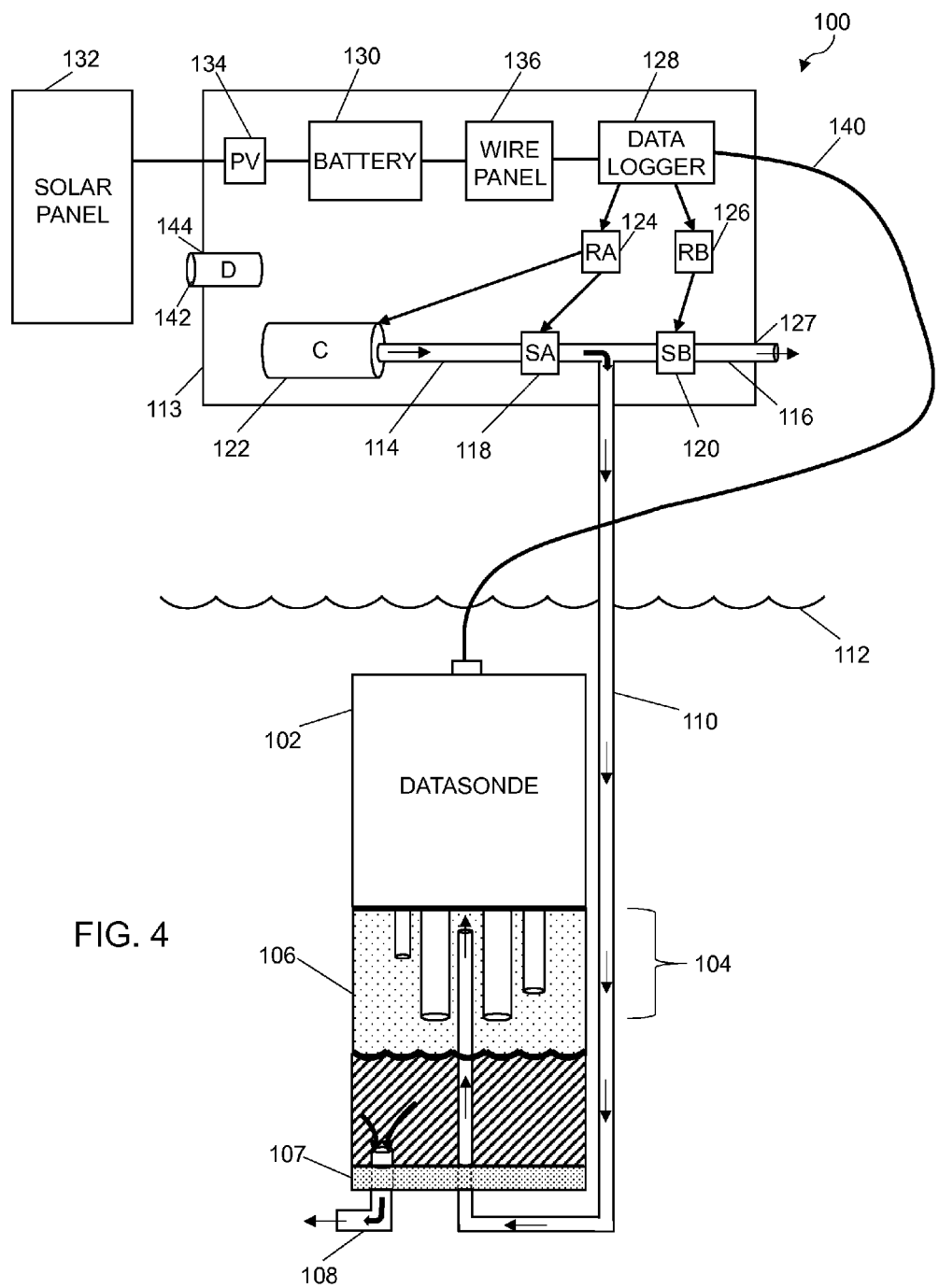
FIG. 4 illustrates the aquatic monitoring apparatus of FIG. 3 immediately after a sample time where the sample chamber is being purged of water.

FIG. 4 illustrates the aquatic monitoring apparatus 100 as the ambient water is being purged from the sample chamber 106. Immediately following the sampling event, at the moment sample event data are received by the datalogger 128 from the datasonde 102, the datalogger 128 activates the relay RA 124, which opens the solenoid valve SA 118 and activates the compressed air source C 122, thus forcing compressed air into the sample chamber 106 through the air tube 110. Compressed air is introduced into the sample chamber 106 for approximately two to five seconds, depending on the depth of the datasonde 102 and the pressure of the compressed air source C 122. The compressed air purges the sample chamber 106 of water, which exits the sample chamber 106 through the water tube 108. The solenoid valve SA 118 is closed, and the cycle repeats 14 minutes into the next sample interval.

The aquatic monitoring apparatus 100 described herein provides several advantages including, but not limited to, the following:

(a) deployment intervals are extended and service intervals are reduced, which reduces operational costs;

(b) as the sensor array 104 is not in contact with the ambient water, wear and tear of the sensor array 104 is reduced which reduces maintenance costs, including sensor replacement costs;

(c) the aquatic monitoring apparatus 100 allows turbulent ambient waters to be sampled as entrained gasses are allowed to escape through the air tube 110 into the atmosphere thus eliminating sensor bubble interference;

(d) the aquatic monitoring apparatus 100 reduces the volume of sediment trapped in the sample chamber 106 as sampled waters are turbulently expelled through the water tube 108;

(e) the aquatic monitoring apparatus 100 does not need to rely on biocides, chemical treatments, or pumps to lessen biofouling, thus no pumping or agitation of water occurs as the sample chamber 106 fills, and no pump maintenance is required; and (f) the aquatic monitoring apparatus 100 may be oriented horizontally to operate in as little as approximately 25 cm of water.

While the foregoing written description of the invention enables one of ordinary skill to make and use what is described herein, those of ordinary skill will understand and appreciate the existence of variations, combinations, and equivalents of the disclosed embodiment and method. The invention should therefore not be limited by the above description embodiment, but by all embodiments and methods within the scope and spirit of the invention as disclosed.

What is claimed is:

1. An aquatic monitoring apparatus for use in controlling biofouling of a water sensing device, comprising:
   a water sensing device having a sensor array;
   a sample chamber attached to the water sensing device and enclosing the sensor array;
   a water tube projecting out of the sample chamber and into a body of water to be sampled;
   an air tube having a first end projecting into the sample chamber and a second end extending above the body of water;
   an air source connected to the second end of the air tube; and
   a controller connected to the water sensing device and the air source to control the water sensing device, the air source, and sampling of the water during sample cycles, wherein the controller operates the water sensing device to sample the water after the water enters and fills the sample chamber through the water tube and contacts the sensor array while air inside the sample chamber escapes into the atmosphere through the air tube, and wherein once the water has been sampled, the controller activates the air source for two to five seconds to force air into the sample chamber through the air tube to purge the sample chamber of the water through the water tube so that the sensor array does not remain immersed in biofouled water.

2. The aquatic monitoring apparatus of claim 1, further comprising an end cap at a bottom of the sample chamber with a first port and a second port, wherein the sample chamber is plumbed with the water tube and the air tube through the first port and the second port, respectively.

3. The aquatic monitoring apparatus of claim 1, wherein the air tube at the second end splits into a first line and a second line, the air source being connected to a terminus of the first line.

4. The aquatic monitoring apparatus of claim 3, further comprising a first solenoid valve connected to the first line between the air source and the second line, and a second solenoid valve connected to the second line, a terminus of the second line being open to the atmosphere.

5. The aquatic monitoring apparatus of claim 4, further comprising a first relay switch disposed between the controller and the first solenoid valve and a second relay switch disposed between the controller and the second solenoid valve,
   wherein the controller activates the second relay switch to open the second solenoid valve and allow the water to enter the sample chamber through the water tube while the air inside the sample chamber escapes into the atmosphere through the second line of the air tube, and the controller deactivates the second relay switch to close the second solenoid valve after the sample chamber has filled with water so that the water remains in the sample chamber during sampling, and
   wherein the controller, after the water has been sampled and to control biofouling, activates the first relay to open the first solenoid valve and activate the air source and force air into the sample chamber through the air tube which purges the sample chamber of water through the water tube, and the controller deactivates the first relay switch to close the first solenoid valve after the water has been purged so that the sensor array does not remain surrounded by biofouled water during time when, the water is not being sampled.

6. The aquatic monitoring apparatus of claim 1, wherein the water sensing device is a datasonde.

7. The aquatic monitoring apparatus of claim 1, wherein the air source is an air compressor.

8. The aquatic monitoring apparatus of claim 1, wherein the air source is a compressed air tank.

9. The aquatic monitoring apparatus of claim 1, wherein the controller is a datalogger.

10. The aquatic monitoring apparatus of claim 1, further comprising a power source connected to the controller and to a solar panel.

11. The aquatic monitoring apparatus of claim 10, wherein the power source is a battery.

12. A method for controlling biofouling of a water sensing device, comprising:
   providing a water sensing device having a sensor array;
   attaching a water-tight sample chamber to the water sensing device that encloses the sensor array;
   providing a water tube that projects out of the sample chamber and into a body of water to be sampled;
   providing an air tube that projects out of the sample chamber and extends above the body of water;
   filling the sample chamber to sample the body of water, by allowing the water to enter the sample chamber through the water tube and contact the sensor array while air inside the sample chamber escapes into the atmosphere through the air tube;
   controlling biofouling once the water has been sampled by forcing air into the sample chamber through the air tube for two to five seconds which purges the sample chamber of the water through the water tube so that the sensor array does not remain immersed in biofouled water; and
   repeating said filling and said controlling as desired to take additional samples.

13. The method of claim 12, further comprising:
   splitting an end of the air tube above the body of water into a first line and a second line;
   connecting an air source to a terminus of the first line;
   connecting a first solenoid valve to the first line between the air source and the second line, opening a terminus of the second line to the atmosphere, and connecting a second solenoid valve to the second line between the terminus of the second line and the first line; and
   providing a controller and connecting a first relay switch between the controller and the first solenoid valve and a second relay switch between the controller and the second solenoid valve.

14. The method of claim 13, wherein said filling the sample chamber to sample the body of water further comprises:
   activating, by the controller, the second relay switch to open the second solenoid valve and allow the water to enter the sample chamber through the water tube, which enables the air inside the sample chamber to escape into the atmosphere through the second line of the air tube; and
   deactivating, by the controller, the second relay switch to close the second solenoid valve after the sample chamber has filled with water so that the water remains in the sample chamber during sampling.

15. The method of claim 14, wherein said controlling biofouling once the water has been
   sampled further comprises:
   activating, by the controller, the first relay to open the first solenoid valve and activate the air source, the air source forcing air into the sample chamber through the air tube which purges
   the sample chamber of water through the water tube; and
   deactivating, by the controller, the first relay switch to close the first solenoid valve after the water has been purged so that the sensor array does not remain surrounded by biofouled water during time when the water is not being sampled.

16. A method for using water measuring probes of a water sensing device to measure predetermined characteristics of water proximate to said probes, said method comprising:
   providing a water-sealed sampling chamber enclosing said probes from said water proximate to said water sensing device, said sampling chamber being constructed to be submerged in a body of water of which said predetermined characteristics of water are to be measured;
   providing an air tube that connects said sampling chamber to outside air above said body of water and enables a flow of air between said sampling chamber and said outside air above said body of water;
   providing a compressed air input device connected to a first end of the air tube for selectively forcing air into said sampling chamber for two to five seconds, while venting air to the outside air through a second end of the airtube; and
   controlling an amount of air in said sampling chamber through a controller connected to said compressed air device and said water sensing device wherein water is only in contact with said probes when said probes are measuring said predetermined characteristics of water in said sampling chamber.

17. The method as set forth in claim 16 wherein said sampling chamber is vented to outside air by operating a valve device to allow water to selectively flow into and out of said sample chamber when said water sensing device is under water.

18. The method as set forth in claim 17 wherein said valve device is normally closed and selectively opened to allow water into said sampling chamber at predetermined times.

19. The method as set forth in claim 18 and further including selectively evacuating water from said sampling chamber after said probes have completed measuring said predetermined characteristics of water in said sampling chamber.

* * * * *